United States Patent [19]
Silvian

[11] Patent Number: 6,096,062
[45] Date of Patent: Aug. 1, 2000

[54] METHOD AND APPARATUS FOR MAINTAINING A HIGH VOLTAGE CAPACITOR IN AN IMPLANTABLE CARDIAC DEVICE

[75] Inventor: Sergiu Silvian, La Crescenta, Calif.

[73] Assignee: Pacesetter, Inc., Sylmar, Calif.

[21] Appl. No.: 09/093,505

[22] Filed: Jun. 8, 1998

[51] Int. Cl.[7] .................................................... A61N 1/37
[52] U.S. Cl. ................................................................ 607/5
[58] Field of Search ............................................ 607/5–8

[56] References Cited

U.S. PATENT DOCUMENTS

| | | |
|---|---|---|
| 5,113,862 | 5/1992 | Mortazavi . |
| 5,414,475 | 5/1995 | Trzyna et al. . |
| 5,499,156 | 3/1996 | Bentley . |
| 5,684,426 | 11/1997 | De Doncker . |
| 5,741,307 | 4/1998 | Kroll ............................................ 607/5 |
| 5,792,188 | 8/1998 | Starkweather et al. ...................... 607/5 |

Primary Examiner—William E. Kamm
Assistant Examiner—George R. Evanisko

[57] ABSTRACT

An implantable cardiac device incorporating a processor and a waveform generation circuit incorporating a high voltage capacitor wherein the processor is adapted to charge the capacitor to an initial voltage, less than the peak voltage, and then measure the leakage current occurring across the capacitor at the initial voltage. If the leakage current occurring across the capacitor at the initial voltage is less than a preselected value, selected so that the corresponding leakage current across the capacitor when the capacitor is charged to the peak voltage is within an acceptable tolerance range, the processor then does not perform any further reforming of the capacitor. Alternatively, if the leakage current across the capacitor at the initial voltage is greater than the preselected value, even the processor is adapted to charge the capacitor to a higher voltage, such as the peak voltage, and retain the capacitor at the higher voltage so that the capacitor may be reformed as a result of the application of the higher voltage.

35 Claims, 3 Drawing Sheets

METHOD AND APPARATUS FOR MAINTAINING A HIGH VOLTAGE CAPACITOR IN AN IMPLANTABLE CARDIAC DEVICE

FIELD OF THE INVENTION

The present invention relates to implantable cardiac devices, such as an implantable cardioverter-defibrillator (ICD) and, more particularly, relates to an apparatus and method for reforming the capacitor of an implantable cardiac device in a more efficient manner.

BACKGROUND OF THE INVENTION

Implantable cardiac devices, such as pacemakers and implantable cardioverter-defibrillators (ICD's), are well-known devices that are adapted to be implanted within the body of patients and provide therapeutic stimulation to the heart to regulate heart function. Present generation devices typically include one or more leads that are adapted to be positioned adjacent the heart, circuitry for generating a therapeutic waveform, sensors which sense the function of the heart, and a processor which receives signals from the sensor and induces the waveform generation circuitry to develop and provide a waveform to the heart via the leads to regulate heart function on an as-needed basis.

An implantable cardioverter-defibrillator is a commonly used implantable cardiac device. The ICD is implanted within the body of the patient and is capable of sensing when the heart is experiencing particular forms of tachycardia requiring cardioversion or defibrillation. In particular, implantable cardioverter-defibrillators are commonly used to end ventricular fibrillation. Typically, these types of ICD's have sensors which are adapted to sense when the ventricle of the heart is fibrillating. Upon sensing the ventricular fibrillation, the processor of the ICD induces the waveform generation circuit to develop a high voltage, typically biphasic, waveform to be applied to the ventricle of the heart via the leads. Typically, the leads include an RV coil that is positioned adjacent the inner walls of the ventricle. The high voltage waveform is adapted to simultaneously depolarize substantially all of the heart cells in the ventricle so that these cells can subsequently repolarize and, preferably, function in a normal fashion. It is presently believed that fibrillation is largely characterized by these spontaneous unorganized discharging of the cells of the ventricle which results in little or no blood being pumped by the ventricle which can result in the death of the patient.

Consequently, it is desirable that ICD's be able to develop and provide the therapeutic waveform very quickly following the detection of such a cardiac event. Similarly, with other tachycardias, it is also desirable that the ICD be able to provide the therapeutic waveform very quickly after the detection of the event so as to minimize discomfort to the patient and also so as to reduce the likelihood that a comparatively mild tachycardia will develop into a more serious problem. Hence, the ability to quickly generate the waveform upon sensing the cardiac event is a serious design constraint of implantable cardiac devices like ICD's.

A further design constraint of these types of devices is that the device is typically powered by a battery implanted within the body of the patient. Consequently, it is desirable to conserve the limited energy of the battery as much as possible so as to increase the longevity of the device. Replacement of batteries can involve an invasive surgical procedure to access the implanted battery.

In order to conserve battery power, the capacitors that produce the defibrillation or cardioversion waveform are left in an uncharged state when not in use. The capacitors are then only charged when a cardiac event is detected. Leaving the capacitors in an uncharged state during periods of non-use reduces the overall drain on the battery and thereby conserves more of the limited battery energy for the generation of therapeutic waveforms during cardiac events.

However, leaving the capacitors in an uncharged state during the time intervals between the application of therapeutic waveforms to the heart can result in the capacitor degrading over time. Typically, the high voltage capacitors that are used in implantable cardiac devices, such as ICD's, are electrolytic high voltage capacitors that have an oxide dielectric. In the absence of a voltage being applied across the plates of the capacitor, the oxide dielectric can degrade over time. Subsequently, when the capacitor is charged, there can be a considerable leakage current occurring between the two plates of the capacitor as a result of the degradation of the dielectric.

This leakage current can prolong the time that it takes to charge the capacitor to the voltage necessary to produce the therapeutic waveform thereby delaying the delivery of the therapeutic waveform to the heart. In applications such as ventricular defibrillation, any delay in the application of the waveform to the heart can result in disastrous consequences for the patient. Moreover, this leakage current also requires that more energy be expended to charge the capacitor to the desire level to be able to apply the therapeutic waveform to the heart. Consequently, the leakage current can further result in excessive consumption of limited battery power thereby decreasing the longevity of the implanted device.

To address the particular problem of the capacitors of the implantable cardiac devices degrading during extended periods of non-use, implantable cardiac devices of the prior art have been adapted to periodically charge the capacitors during these extended periods of non-use. For example, it is a common practice to charge the capacitor to its maximum voltage at regular intervals, e.g., one to three months, if no shocks have been delivered during this period. While this process has the effect of reducing the degradation of the capacitor dielectric during the period of non-use, this practice is a considerable drain on the battery and can significantly reduce the total number of therapeutic waveforms that can be provided by the implanted cardiac device.

For example, for a typical capacitor used in an ICD, the capacitor will be charged during reforming maintenance to approximately 800 volts which requires the battery to provide approximately 55 joules of energy. This is a considerable expenditure of the battery's energy which significantly reduces the longevity of the battery. Moreover, the prior art systems that periodically charge the capacitors often end up charging the capacitors when dielectric has not degraded to the point where the leakage current that would occur during the generation of a therapeutic waveform would present a problem. Consequently, while periodically reforming the capacitor during periods of non-use to the capacitor's peak voltage may reduce the leakage current during therapeutic waveform generation, the reduction in leakage current is accomplished at a significant cost in terms of battery and device longevity.

Hence, there is a need for an implantable cardiac device, such as an ICD, that is capable of reforming the capacitors that provide the therapeutic waveform in a more efficient manner. To this end, there is a need for an implantable cardiac device which is capable of maintaining the capacitors in a condition such that the leakage current of the capacitor on charging is kept within acceptable tolerances without requiring a considerable expenditure of the limited energy provided by the battery of the device.

SUMMARY OF THE INVENTION

The aforementioned needs are satisfied by the implantable cardiac device of the present invention which is comprised of at least one lead that is adapted to be positioned adjacent the heart so as to provide a therapeutic waveform to the heart, a waveform generation circuit which includes at least one capacitor that is adapted to develop a therapeutic waveform to be supplied to the heart via the at least one lead, and a processor that induces the waveform generation circuit to generate the waveform by charging the capacitor to a desired voltage level. The processor is adapted to periodically induce the waveform generation circuit to charge the capacitor to a first voltage, less than the desired voltage, and the processor further obtains a measurement indicative of leakage current of the capacitor occurring at the first voltage. The processor then ascertains whether the leakage current measurement indicates that when the capacitor is charged to the desired voltage, the leakage current occurring at the desired voltage level is less than a preselected limit. As the first voltage is less than the desired voltage, the amount of energy needed to charge the capacitor to determine if the capacitor has undesirably degraded is reduced.

In one aspect of the invention, the processor is adapted to further induce the waveform generation circuit to charge the capacitor to a voltage level higher than the first voltage upon determining the first measurement indicates that the leakage current that would occur if the capacitor is charged to the desired voltage would be unacceptably high. Charging the capacitor to a higher voltage level can have the effect of reforming the capacitor so as to reduce the leakage current that would occur when the capacitor is charged to produce the therapeutic waveform. The processor can be further adapted to perform this function at periodic intervals during extended periods of non-use of the waveform generation circuit. Hence, the leakage current of the capacitor can be periodically measured at a lower voltage level, thereby conserving battery energy, and the capacitor will only need to be charged to a higher voltage level to reform the capacitor when the measurement indicates that the leakage current of the capacitor when charged to generate the therapeutic waveform would be too large.

In another aspect of the invention, a method of maintaining a capacitor comprising a portion of an implantable cardiac device is provided. The method comprises charging the capacitor of the implantable cardiac device to a first voltage level less than a desired voltage level to which the capacitor will be charged when the waveform is to be delivered to the heart, obtaining a measurement indicative of the leakage current at the first voltage level, and determining whether the measurement at the first voltage level indicates that the leakage current at the desired voltage level would be too high. In one embodiment, the method can further comprise charging the capacitor to a second voltage level greater than the first voltage level to reform the capacitor upon determining that the measurement at the first voltage level would indicate that the leakage current that would occur if the capacitor was charged to the desired voltage level would be too high.

The present invention therefore provides a way of maintaining and reforming capacitors in implanted cardiac devices so as to reduce the leakage current that would occur when the capacitors are charged to produce the therapeutic waveform in a manner that reduces the overall drain on the battery during the reforming and maintenance process. These and other objects and advantages of the present invention will become more fully apparent from the following description taken in conjunction with the accompanying drawings.

DETAILED DESCRIPTION OF THE PREFERRED EMBODIMENT

Figure 1:
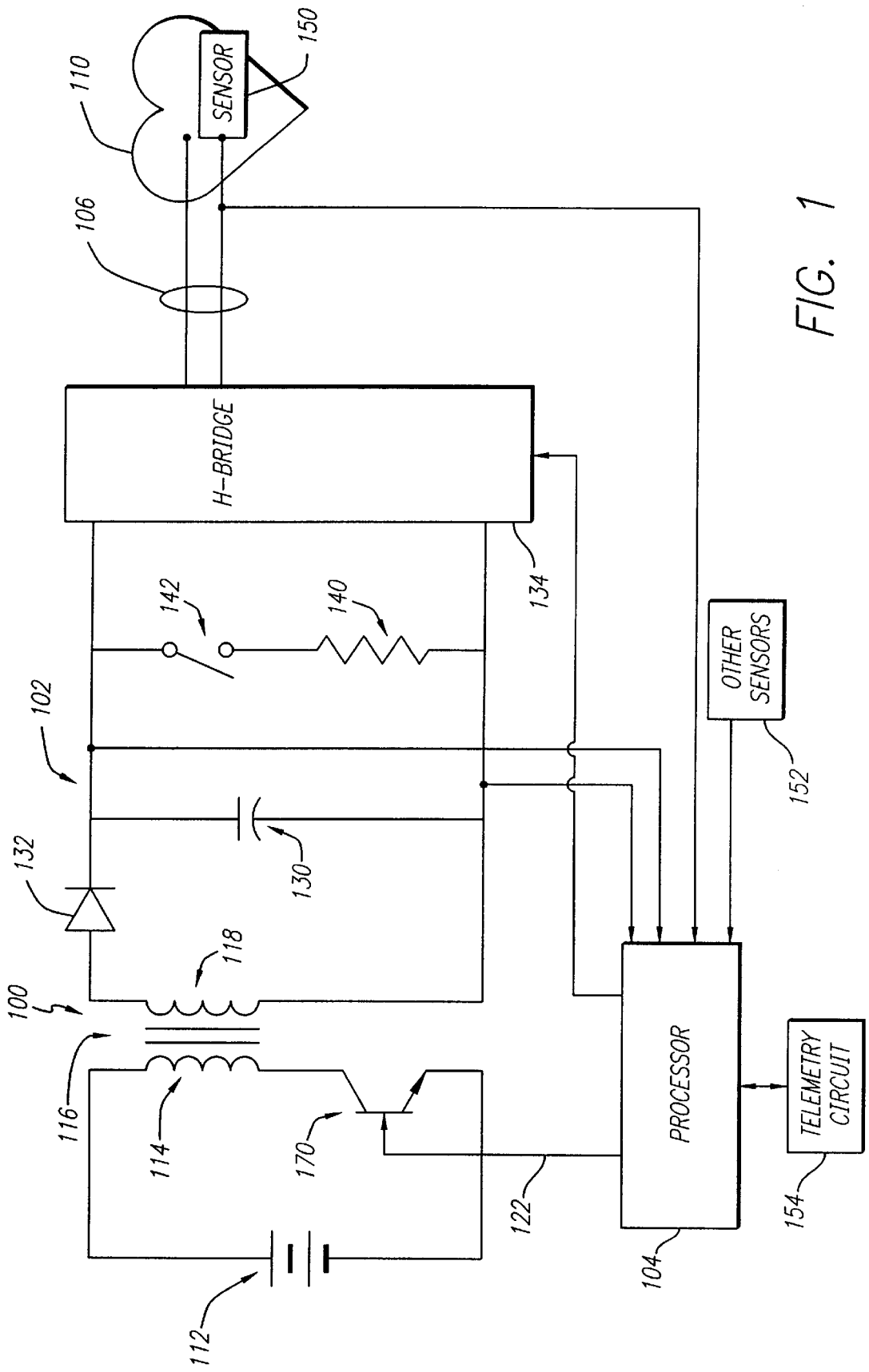
FIG. 1 is a simplified block diagram of a typical implantable cardiac device having a processor and a capacitor that is charged to a desired voltage level in order to apply a therapeutic waveform to the heart of a patient.

Reference will now be made to the drawings wherein like numerals refer to like parts throughout. Referring initially to FIG. 1, a simplified block diagram of an exemplary implantable cardiac device 100 is illustrated. The implantable cardiac device 100 includes a waveform generation circuit, generally designated 102, a processor 104 and at least one lead 106 that is adapted to provide a therapeutic waveform developed by the waveform generation circuit 102 to a heart 110 of a patient.

As is understood in the art, the waveform generation circuit 102 and the processor 104 are typically contained within a casing (not shown) that is adapted to be implanted within the body of the patient. One typical type of implantation is known as a pectoral implant where the casing containing the waveform generation circuit 102 and the processor 104 and any other associated circuitry is implanted in the body of the patient underneath the pectoral muscle. The casing can also be adapted to provide the return electrode of the implantable cardiac device.

The leads 106 are further adapted to be implanted within the body of the patient so that the lead tips are positioned adjacent the heart 110 in a manner that will allow the leads to deliver the therapeutic waveform to the heart. One typical lead configuration adapted for cardioversion or defibrillation purposes comprises positioning an RV coil within the ventricle of the heart so that the walls of the heart can receive a defibrillation waveform from the RV coil in a well-known manner.

FIG. 1 illustrates a waveform generation circuit 102 that has been simplified for the purposes of clarity. Specifically, the waveform generation circuit 102 includes a battery 112 that is adapted to supply energy to all of the components of the implantable cardiac device 100. The outputs of the battery 112 are typically connected to the primary winding 114 of a transformer 116. A switch, such as a transistor 120, is preferably connected to the transformer 116 so that actuation of the transistor 120 results in the primary winding 114 being energized by the battery 112. The transistor 120 is preferably controlled by a control line 122 emanating from the processor 104 that is connected to the gate of the transistor 120. In this manner, the processor 104 can energize the primary winding 114 of the transformer 116 by sending a high signal on the control line 122 to the gate of the transistor 120.

Energizing the primary winding 114 of the transformer 116 results in a charging voltage appearing on the secondary winding 118 of the transformer 116. The charging voltage on the secondary winding 118 is preferably provided to at least one high voltage capacitor 130 through a rectifying diode 132 so as to charge the capacitor 130 to a desired voltage level.

Subsequently, the voltage from the capacitor 130 can be provided to the leads 106, preferably via an H-bridge 134. The H-bridge 134 is controlled by the processor 104 so that a biphasic waveform can be applied to the heart 110 via the leads 106. The waveform generation circuit 102 may also include a shunt resistor 140 that is connected in parallel with the capacitor 130 via a switch 142 that is preferably under the control of the processor 104 so that the switch 142 can be periodically closed such that voltage in the capacitor 130 can be discharged through the shunt resistor 140.

The implantable cardiac device 100 may also include a sensor 150 that provides a signal to the processor 104 that is indicative of the function of the heart. In one embodiment, the sensor 150 can be comprised of one of the leads 106 that is implanted within a chamber of the heart so that the processor can receive an intracardiac electrogram (IEG) signal that is indicative of the function of the heart. The processor 104 may also receive other signals from other sensors 152 such as activity sensors and the like. The processor 104 may also be able to communicate with an external programmer (not shown) via a telemetry circuit 154 in a well-known manner.

The circuit diagram of FIG. 1 illustrates a simplified implantable cardiac device, such as an implantable cardioverter-defibrillator (ICD). This device is capable of detecting when the heart 110 is having a cardiac event, such as ventricular fibrillation, and can then induce the waveform generation circuit to produce a high voltage waveform that is to be applied to the heart 110 via the leads 106 in an effort to correct the function of the heart 110. The operation of the implanted cardiac device loo during the delivery of therapeutic waveforms is substantially similar to prior art implantable cardiac devices.

Specifically, the processor 104, upon receiving a signal from the sensor 150 indicating that a cardiac event, such as ventricular fibrillation, is occurring, sends a signal on the control line 122 so that the transistor 120 is pulsed on thereby energizing the primary winding 114 of the transformer 116. The resulting voltage on the secondary winding 118 of the transformer 116 is then provided to the capacitor 130 so as to charge the capacitor 130 to a desired voltage level. The desired voltage may vary depending upon the configuration of the implantable cardiac device 100 and the particular cardiac event which the implantable cardiac device 100 is adapted to correct. For example, if the implantable cardiac device 100 is adapted to correct ventricular fibrillation, the capacitor 130 may be charged to the order of 800 volts.

Upon the capacitor being charged to the desired voltage, the processor 104 manipulates the H-bridge 134 so that a positive portion of a biphasic waveform can be provided to the leads 106 for subsequent delivery to the heart 110. The processor 104 is further adapted to manipulate the H-bridge 134 in a known manner so that a negative portion of the waveform can also be applied to the heart 110 via the leads 106. On occasion, the capacitor 130 may be charged, but the processor 104 will determine not to apply the waveform to the heart 110. In this circumstance, the switch 142 can be closed and the voltage on the capacitor 130 can be discharged through the shunt resistor 140.

In this manner, the implantable cardiac device 100 is capable of providing therapeutic waveforms to the heart 110. The configuration of the waveform generation circuit 102 will, of course, vary depending upon the type of waveform that is to be provided to the heart 110. However, the waveform generation circuits 102 typically include at least one high voltage capacitor that is periodically charged. In this embodiment, the capacitor 130 is periodically maintained and reformed by the processor 104 and it will be appreciated from the following description that the maintenance and reforming process of the capacitor of the present invention can be applied to any of a number of different configurations of waveform generation circuits without departing from the present invention.

In particular, it is desirable that the therapeutic waveform be delivered to the heart 110 as quickly as possible after the processor 104 has ascertained that a cardiac event, such as ventricular fibrillation, is occurring. If the capacitor 130 has not been charged for an extended period of time, there may be substantial leakage current through the dielectric of the capacitor 130 when the capacitor 130 is charged by the secondary winding 118 of the transformer 116 to generate the therapeutic waveform. This leakage current can result in the capacitor 130 being charged over too long of a period of time delaying the delivery of the therapeutic waveform to the heart 110.

To address this particular problem, the processor 104 periodically charges the capacitor 130 to a reduced voltage and measure the resulting leakage current and ascertain whether the measured leakage current at the reduced voltage indicates that the leakage current that would occur when the capacitor 130 is charged to the desired voltage needed to generate the therapeutic waveform exceeds a desired limit. If the measured leakage current indicates that the expected leakage current at the desired voltage exceeds the desired limit, the processor 104 then charges the capacitor 130 to a higher voltage so as to reform the capacitor 130 and reduce the expected leakage current occurring when the capacitor is charged to the desired voltage to deliver the therapeutic waveform to the heart. In this way, the processor 104 can reduce the amount of leakage current that would occur during charging of the capacitor 130 when a therapeutic waveform is to be delivered, but do so in a manner that reduces the amount of energy that must be provided by the battery 112 to periodically reform the capacitor 130.

Figure 2A:
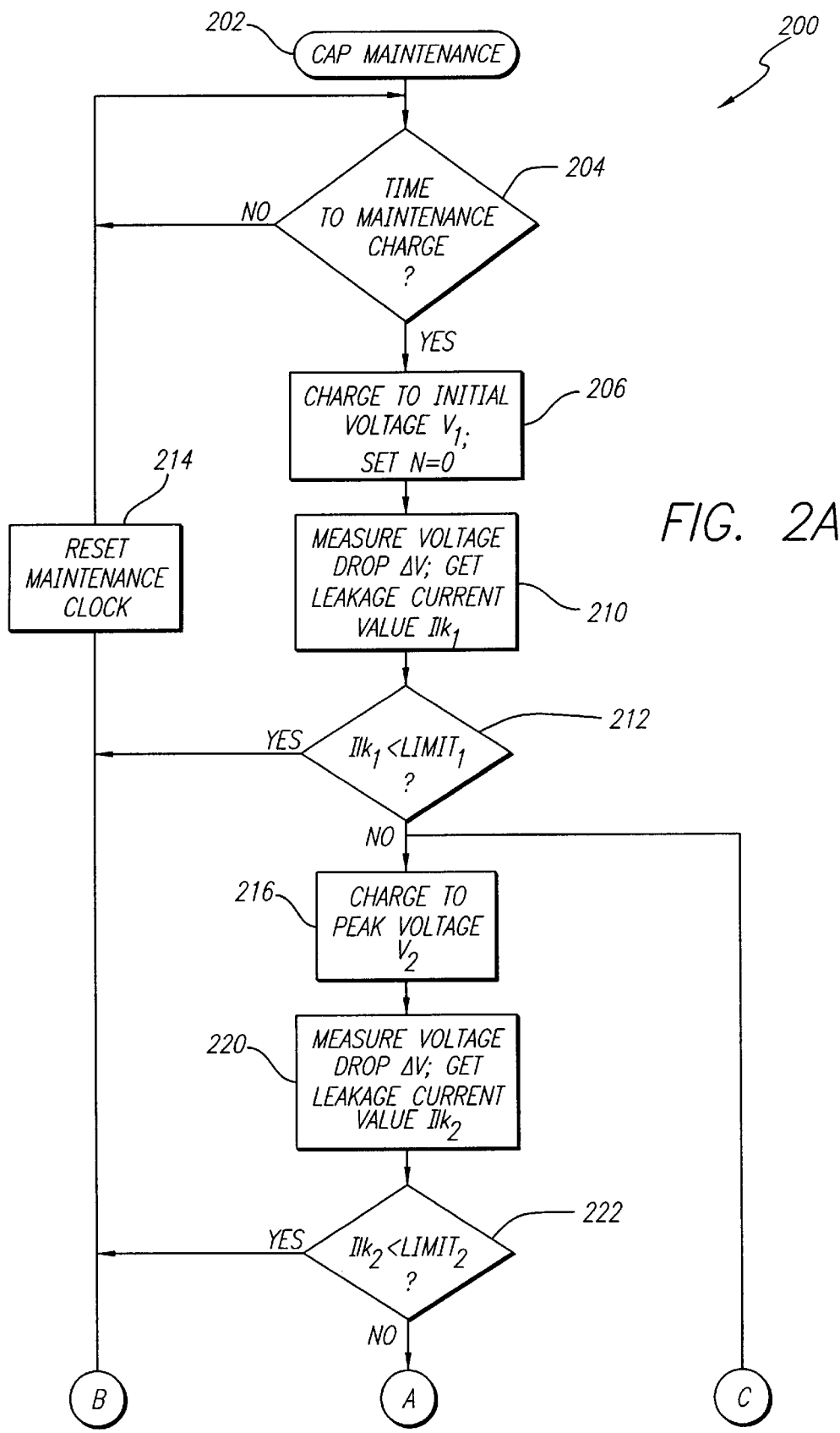
FIGS. 2A AND 2B comprise an exemplary flowchart of a capacitor maintenance process performed by the processor of the implantable cardiac device of FIG. 1 when the processor is engaged in reforming the capacitor to reduce the amount of leakage current that would occur when the capacitor is charged to the desired voltage level to produce a therapeutic waveform to be delivered to the heart of the patient.
Figure 2B:
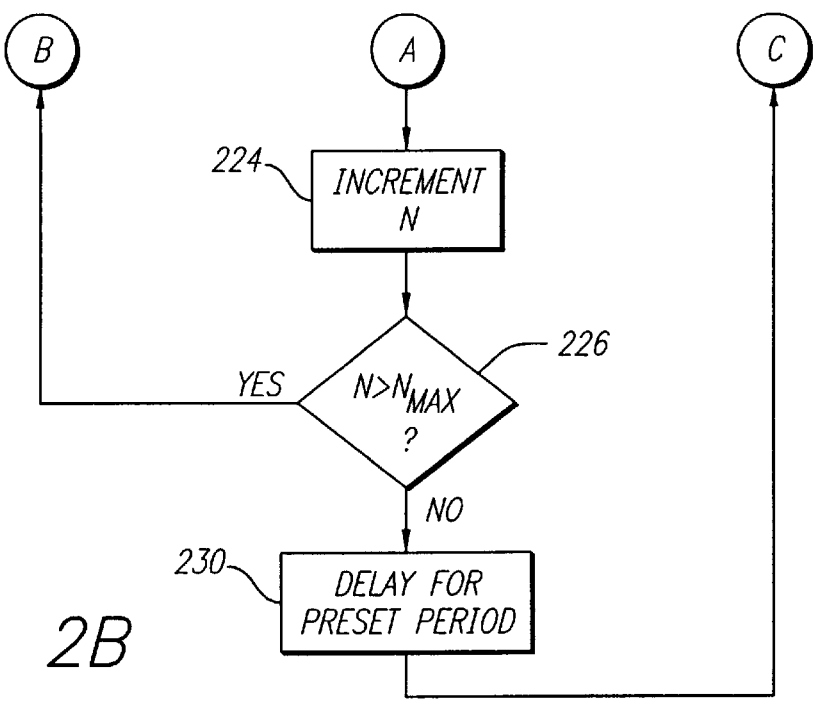

FIGS. 2A AND 2B comprise an exemplary flowchart which essentially illustrates a capacitor maintenance process implemented by the processor 104 to maintain the capacitor 130. The processor 104 in this embodiment is adapted to periodically undertake the capacitance maintenance process 200 illustrated in FIGS. 2A AND 2B. The purpose of this process 200 is to ensure that the capacitor 130 will be maintained in a condition where the leakage current that occurs when the capacitor 130 is charged to deliver the therapeutic waveform the patient is kept within an acceptable range.

Initially, from a start state 202, the processor 104 determines, in decision state 204, whether the time period for assessing the status of the capacitor 130 has occurred. In this embodiment, the processor 104 is adapted to assess the leakage current status of the capacitor 130 at periodic intervals selected so that the capacitor 130 can be maintained at a high degree of readiness for subsequent delivery of the therapeutic waveform to the patient. For example, the processor 104 may be adapted to test the leakage current status of the capacitor 130 on a monthly or bimonthly basis during any extended period of time where the waveform generation circuit 102 is not called upon to generate a therapeutic waveform for delivery to the heart 110 to correct a cardiac event.

If the processor 134 determines, in decision state 204, that it is time to test the leakage current status of the capacitor 130, the processor 104 then proceeds to charge the capacitor to an initial voltage $V_1$ in state 206. The charging of the capacitor 130 to $V_1$ is accomplished by the processor 104 applying a signal on line 122 so that transistor 120 (FIG. 1) is pulsed on, thereby the primary winding 114 of the transformer 116 is energized by the battery 112. The secondary winding 118 of the transformer 116 then charges the capacitor 130 to the voltage $V_1$. The processor 104 samples the voltage across the capacitor 130 so that, when the capacitor 130 is charged to the voltage $V_1$, the processor 104 disables the transistor 120 thereby halting the charging of the capacitor 130. The voltage $V_1$ is preferably selected to as to be less than the voltage that the capacitor 130 is charged to when the waveform generation circuit 102 is generating a therapeutic waveform to be delivered to the heart 110.

In one exemplary implantable cardiac device, the capacitor 130 is charged to approximately 800 volts when the waveform generation circuit is developing the therapeutic waveform that is to be applied to the heart 110. In that example, the processor 104 in the capacitor maintenance process 200 charges the capacitor 130 to a voltage $V_1$ of approximately 100 volts, drawing only 1/64 of the energy required to charge to 800 volts.

Once the processor 104 has charged the capacitor 130 to the initial voltage $V_1$, the processor 104, in state 206, then sets a counter variable N equal to zero and measures the voltage drop over a preselected interval of time following the charging of the capacitor 130 to the initial voltage $V_1$. As illustrated in FIG. 1, the processor 104 samples the voltage across the plates of the capacitor 130 and can be induced to sample the voltage across the plates of the capacitor 130 a preselected time period after the capacitor 130 has been charged to the initial voltage $V_1$. The change in voltage $\Delta V$ can then be used to calculate the leakage current $I_{lk1}$ occurring across the capacitor 130 when the capacitor is charged to the initial voltage $V_1$.

Figure 3:
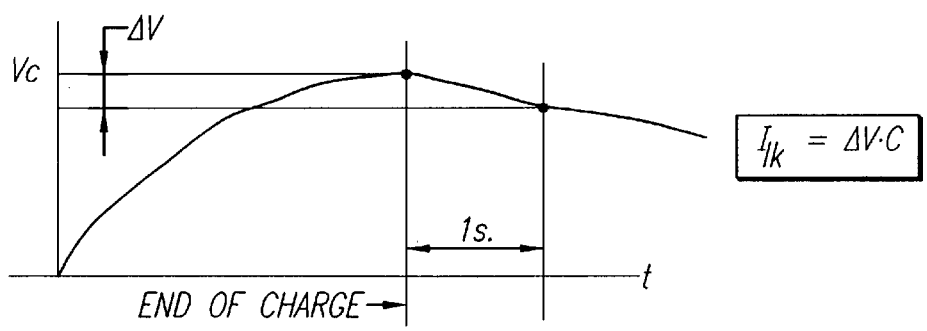
FIG. 3 is a diagram illustrating how the processor determines a leakage current parameter during the performance of the capacitor maintenance process of FIGS. 2A AND 2B.

Specifically, FIG. 3 illustrates that if the change in voltage $\Delta V$ following the charging of the capacitor 130 to the initial voltage $V_1$ is measured over a one second interval, then the measured leakage current $I_{lk1}$ is simply the change in voltage $\Delta V$ times the capacitance of the capacitor 130. In one embodiment, the capacitor 130 has a capacitance value of approximately 100 $\mu F$. A $\Delta V=5V$ will compute to $I_{lk1}=500$ $\mu A$.

Once the leakage current value $I_{lk1}$ is determined in state 210, the processor 104 then compares the leakage current $I_{lk1}$ to a limit value, $LIMIT_1$, in decision state 212. The limit value, $LIMIT_1$, is preferably empirically selected so that if the measured leakage current $I_{lk1}$ occurring across the plates of the capacitor 130 at the initial voltage $V_1$ is less than the limit value, $LIMIT_1$, then the expected leakage current that will occur across the plates of the capacitor 130 when the capacitor 130 is charged to the desired voltage for the delivery of the therapeutic waveform to the heart will also be within an acceptable limit.

The relationship between the leakage current $I_{lk1}$ occurring at the initial voltage $V_1$ and the leakage current that will occur when the capacitor 130 is charged to a higher desired voltage for generation of the therapeutic waveform at two different voltages using these types of capacitors is not always readily susceptible to quantification by formula. However, by testing of capacitors a limit value can be obtained for the leakage current at the initial voltage $V_1$ which would be indicative of a leakage current value at the desired voltage which is within the tolerance range of the implanted cardiac device 100.

Consequently, if the processor 104 has determined, in decision state 212, that the measured leakage current $I_{lk1}$ occurring when the capacitor 130 is charged to the initial voltage $V_1$ is less than the selected limit, $LIMIT_1$, then the processor 104 proceeds to reset the maintenance clock in state 214 and wait for the next leakage current measurement interval. Hence, if the measured leakage current $I_{lk1}$ at the initial voltage $V_1$ is within the preselected range for this leakage current parameter, then the capacitor 130 is not in need of any additional maintenance of charging to reduce the leakage current that would occur when the capacitor 130 is charged to a desired voltage when the therapeutic waveform is being developed. Consequently, a higher reforming voltage does not need to be applied to the capacitor at this time and the battery energy needed to reform the capacitor 130 at a higher voltage is thereby saved.

Alternatively, if the measured leakage current $I_{lk1}$ occurring at the initial voltage $V_1$ is greater than the maximum permissible leakage current, $LIMIT_1$, for the voltage $V_1$, the processor 104, in state 216, then charges the capacitor 130 to a higher voltage. Specifically, in state 216, the processor 104 charges the capacitor 130 to the voltage $V_2$ which, in one embodiment is substantially equal to the desired voltage, by pulsing the transistor 120 on so as to energize the primary winding 114 of the transformer 116 with energy from the battery 112. The voltage on the secondary winding 118 of the transformer 116 is then applied across the plates of the capacitor 130 until the capacitor 130 reaches the voltage $V_2$. At which time, the processor 104 deactivates the transistor 120.

By charging the capacitor 130 to the voltage $V_2$, the capacitor 130 may be reformed such that the degradation of the oxide dielectric between the plates of the capacitor 130 can be reversed. More particularly, the degradation of the oxide dielectric can often be reversed by the application of voltage to the capacitor 130. By applying a voltage $V_2$ to the capacitor 130, the dielectric may be reformed so that the leakage current that would occur when the capacitor 130 is charged to produce the therapeutic waveform during a cardiac event is reduced to within acceptable limits.

In this embodiment, the voltage $V_2$ is the same voltage to which the capacitor 130 is charged when the capacitor 130 is being charged to generate the therapeutic waveform. However, it will be appreciated that in some instances reformation may occur more efficiently at voltages less than or more than the voltage level needed for the therapeutic waveform. Consequently, the voltage $V_2$ can be any of a range of voltages that is adapted to reform the capacitor 130.

The processor 104, in state 220, then measures the voltage drop $\Delta V$ over a preselected time interval after the capacitor 130 has been charged to the voltage $V_2$. The voltage drop $\Delta V$ is used to obtain the current leakage current value $I_{lk2}$ in the same manner as described above in reference to FIG. 3.

The processor 104 then determines, in decision state 222, whether the leakage current value $I_{lk2}$ for the capacitor 130, when the capacitor 130 is charged to the voltage $V_2$, is less than a preselected limit value, $LIMIT_2$, for the leakage current $I_{lk1}$ at the voltage $V_2$. In this embodiment, the leakage current limit value $LIMIT_2$ is selected to be the maximum permissible leakage current that can occur during the charging of the capacitor 130 to deliver the therapeutic waveform to the heart 110 during a cardiac event. The limit value $LIMIT_2$ is therefore selected so that the capacitor 130 will charge to the desired voltage necessary to deliver the therapeutic waveform to the heart 110 within an acceptable period of time.

If the measured leakage current $I_{lk2}$ occurring when the capacitor 130 is charged to the peak voltage $V_2$ is less than the limit value, $LIMIT_2$, then charging the capacitor 130 to the peak voltage $V_2$, in state 216, has reformed the capacitor 130 sufficiently so that the leakage current that will occur during charging of the capacitor 130 during the generation of a therapeutic waveform will be within an acceptable limit. The processor 104 will then reset the maintenance clock, in state 214, and wait until the current leakage measurement interval has elapsed.

However, if the measured leakage current $I_{lk2}$ occurring across the capacitor 130 when the capacitor 130 is charged to the voltage $V_2$ is greater than the maximum permissible leakage current, $LIMIT_2$, the processor 104 then proceeds to supplementally charge the capacitor 130 in an effort to reform the capacitor 130 sufficiently to reverse the degradation of the dielectric in the capacitor 130. Specifically, the processor 104 proceeds to increment the counter value N, in state 224, and then, in decision state 226, determine whether the capacitor 130 has been supplementary charged more than a maximum permissible number of times $N_{max}$.

If the capacitor 130 has not been supplementary charged a preselected number of times, the processor 104 then proceeds to a delay state 230 where the capacitor 130 is left charged at the higher voltage $V_2$ for a preselected period of time. For example, in one embodiment, the capacitor 130 is left at the higher voltage $V_2$ for approximately an hour so that the capacitor 130 will slowly discharge due to its leakage current. This leakage current will further reform the capacitor. At the end of the delay period 230, the processor 104 then recharges the capacitor to the higher voltage $V_2$, in state 216, in the same manner as described above.

This supplementary charging process comprised of the states 216 through 230, is repeated until either the measured leakage current $I_{lk2}$ in state 220 is less than the limit value, $LIMIT_2$, or until the number of supplementary recharge cycles N is equal to the maximum amount of recharge cycles as determined in decision state 226. In this way, the capacitor 130 can be reformed by the extended application of the voltage $V_2$.

Alternatively, if the capacitor 130 is incapable of being reformed within a selected number of supplementary charging cycles, the recharging process is ended to conserve the energy of the battery 112. In this case, the processor 104 may be further adapted to store in memory a notation of the status of the capacitor 130 so that this status can be provided to a treating physician via the telemetry circuit 154 during follow-up treatment. It will be appreciated that a capacitor 130 that cannot be reformed sufficiently to reduce the leakage current during generation of a therapeutic waveform to within acceptable limits may pose a danger for the patient.

The capacitor 130 can therefore be reformed in a manner where the amount of energy used to reform the capacitor 130 from the battery 112 is reduced. Specifically, the capacitor 130 is only recharged to the voltage $V_2$ when the charging of the capacitor to a lower initial voltage $V_1$ results in a measured leakage current $I_{lk1}$ that is known to correspond to a leakage current at the desired voltage that would be beyond an acceptable limit.

The capacitor 130 is then charged to the peak voltage $V_2$ only when the measured leakage current $I_{lk1}$ initial voltage $V_1$ indicates that the capacitor 130 is in need of a greater reforming voltage. The leakage current can then be measured again at the higher voltage and, if necessary, the capacitor can be retained in a substantially charged condition so that reforming of the capacitor 130 can occur. The capacitor 130 in this embodiment can also be supplementary charged over an extended period of time in order to reform the capacitor 130. The supplementary charging can occur for a period of several hours without requiring the large amounts of energy from the battery 112 as the capacitor 130 is simply recharged to the peak voltage $V_2$ from the voltage drop occurring as a result of the leakage current.

There is a considerable savings in energy to charge an exemplary capacitor to the lower voltage $V_1$. For example, using a 100 $\mu$F farad capacitor that is charged to 100 volts, the energy consumed would be approximately 0.86 joules. However, charging the capacitor to a desired voltage $V_2$ of 800 volts would consume approximately 55 joules of battery power. In this exemplary embodiment, the maximum acceptable leakage current when the capacitor is charged to deliver the therapeutic waveform to the heart would be 100 $\mu$A and the limit value for the measured leakage current when the capacitor is charged to the voltage $V_1$ of 100 volts would be 1000 $\mu$A. It will be appreciated that the limit values $LIMIT_1$ and $LIMIT_2$ selected for the leakage currents at the voltages $V_1$ and $V_2$ will vary depending upon the type of capacitor used and the maximum acceptable limit current at the desired voltage for the implantable cardiac device.

Consequently, it will be appreciated that the apparatus and method of the preferred embodiment is capable of reforming a capacitor so that the capacitor will have a leakage current that is within an acceptable range when the capacitor is charged for the delivery of a therapeutic waveform to the heart of a patient. The charging can be accomplished in manner which reduces the amount of energy from the battery needed to reform the capacitor. This reduction in the amount of energy used during the capacitance maintenance process, conserves the limited battery energy so that the implantable cardiac device is able to deliver therapeutic waveforms to the heart for a longer period of time.

Hence, although the foregoing description of the preferred embodiments of the present invention has shown, described, and pointed out the fundamental novel features of the invention, it will be understood that various omissions, substitutions and changes in the form of the detail of the apparatus as illustrated, as well as the uses thereof, may be made by those skilled in the art without departing from the spirit of the present invention. Consequently, the scope of the invention should not be limited to the foregoing discussion, but should be defined by the appended claims.

What is claimed is:

1. An implantable cardiac device comprising:
   delivery means for delivering a therapeutic waveform to a patient's heart;
   waveform generation means for generating the therapeutic waveform, wherein the waveform generation means includes a capacitor and a charging circuit for charging the capacitor to a desired voltage when the waveform generation means generates the therapeutic waveform;
   capacitor reforming means for reforming the capacitor so that the leakage current of the capacitor at a desired voltage is less than a first preselected limit, wherein the capacitor reforming means periodically charges the capacitor to a first voltage, less than the desired voltage and obtains a first measurement indicative of the leakage current of the capacitor at the first voltage and wherein the capacitor reforming means is adapted to determine whether the first measurement indicates that the leakage current of the capacitor at the desired voltage exceeds the first preselected limit and if the first measurement indicates that the leakage current that would occur when the capacitor is charged to the desired voltage will exceed the first preselected limit, further charges the capacitor to reform the capacitor.

2. The device of claim 1, wherein the delivery means comprises at least one lead that is adapted to be implanted within the patient so as to deliver a therapeutic waveform to the heart of the patient.

3. The device of claim 2, wherein the at least one lead comprises an RV coil, and wherein the therapeutic waveform produced by the waveform generation means is comprised of a biphasic defibrillation waveform.

4. The device of claim 1, wherein the waveform generation means comprises a waveform generation circuit adapted to be implanted in the body of the patient wherein the waveform generation circuit includes a battery, a transformer and a capacitor wherein the transformer is energized by the battery so that the capacitor is charged.

5. The device of claim 1, wherein the capacitor reforming means comprises a processor adapted to be implanted in the body of the patient, wherein the processor is engaged with the waveform generation means so as to be able to induce the waveform generation means to charge the capacitor.

6. The device of claim 1, wherein the capacitor reforming means induces the waveform generation means to charge the capacitor to a second voltage, greater than the first voltage so as to reform the capacitor upon the capacitor reforming means determining that the first measurement indicates that the leakage current of the capacitor that would occur when the capacitor is charged to the desired voltage exceeds the first preselected limit.

7. The device of claim 6, wherein the capacitor reforming means obtains a second measurement indicative of the leakage current of the capacitor at the second voltage and determines whether the second measurement indicates that the leakage current of the capacitor that would occur when the capacitor is charged to the desired voltage exceeds a second preselected limit.

8. The device of claim 7, further comprising a supplemental charging means for charging the capacitor so as to reform the capacitor when the capacitor reforming means determines that the second measurement indicates that the leakage current of the capacitor that would occur when the capacitor is charged to the desired voltage exceeds the first preselected limit.

9. The device of claim 8, wherein the supplemental charging means retains the capacitor in a charged state for a preselected period of time to reform the capacitor.

10. The device of claim 9, wherein the supplemental charging means retains the capacitor in the charged state for an hour and subsequently induces the capacitor to be recharged to the second voltage so that the capacitor reforming means can obtain another measurement indicative of the leakage current at the second voltage to determine if the second measurement indicates that the leakage current that would occur at the desired voltage still exceeds the first preselected limit.

11. The device of claim 10, wherein the supplemental charging means further includes means for continuing to charge the capacitor until the capacitor second measurement indicates that the leakage current, which would occur if the capacitor is charged to the desired voltage, is less than one of the preselected limit or until a preselected number of chargings have occurred.

12. The device of claim 6, wherein the second voltage is equal to the desired voltage.

13. The device of claim 12, wherein the first voltage is approximately 100 volts, the second voltage is approximately 800 volts, the capacitor has a capacitance value of 100 $\mu$F and the second preselected limit of the leakage current that would occur when the capacitor is charged to the desired voltage is approximately 0.5 mA.

14. An implantable cardiac device comprising:
at least one lead that is adapted to be implanted within a patient so as to be able to deliver a therapeutic waveform to a patient's heart;
a waveform generation circuit adapted to be implanted within the patient wherein the circuit generates the therapeutic waveform, wherein the waveform generation circuit includes a capacitor and a charging circuit for charging the capacitor to a desired voltage when the waveform generation circuit generates the therapeutic waveform; and
a processor adapted to be implanted within a patient that induces the waveform generation circuit to generate the therapeutic waveform, wherein the processor further periodically induces the waveform generation circuit to charge the capacitor to a first voltage, less than the desired voltage, and obtain a first measurement indicative of a leakage current of the capacitor at the first voltage and wherein the processor determines whether the first measurement indicates that the leakage current of the capacitor that would occur when the capacitor is charged to the desired voltage exceeds a first preselected limit.

15. The device of claim 14, wherein the processor induces the waveform generation circuit to charge the capacitor to a second voltage, greater than the first voltage so as to reform the capacitor upon the processor determining that the first measurement indicates that the leakage current of the capacitor that would occur at the desired voltage exceeds the first preselected limit.

16. The device of claim 15, wherein the processor obtains a second measurement indicative of the leakage current of the capacitor at the second voltage and determine whether the second measurement indicates that the leakage current of the capacitor that would occur at the desired voltage exceeds a second preselected limit.

17. The device of claim 16, wherein the second voltage is equal to the desired voltage.

18. The device of claim 17, wherein the first voltage is approximately 100 volts, the second voltage is approximately 800 volts, the capacitor has a value of 100 $\mu$F and the second preselected limit of the leakage current that would occur when the capacitor is charged to the desired voltage is approximately 0.5 mA.

19. The device of claim 16, wherein the processor, upon determining that the second measurement indicates that the leakage current of the capacitor that would occur at the desired voltage exceeds the second preselected limit, implements a supplementary charging process wherein the processor induces the waveform generation circuit to leave the capacitor in a charged state for a preselected period of time to reform the capacitor.

20. The device of claim 19, wherein the processor in the supplementary charging process induces the waveform generation circuit to leave the capacitor in the charged state for an hour and subsequently induces the capacitor to be recharged to the second voltage so that the processor can obtain another measurement indicative of the leakage current at the second voltage to determine if the second measurement indicates that the leakage current that would occur at the desired voltage still exceeds the second preselected limit.

21. The device of claim 20, wherein the processor continues the supplementary charging process until one of the capacitor second measurement indicates that the leakage current that would occur if the capacitor is charged to the desired voltage is less than the second preselected limit or until a preselected number of supplementary charging processes have occurred.

22. The device of claim 14, wherein the at least one lead comprises an RV coil, and wherein the therapeutic waveform produced by the waveform generation circuit is comprised of a biphasic defibrillation waveform.

23. A method of maintaining a capacitor of an implantable cardiac device having a waveform generation circuit, the waveform generation circuit including the capacitor and a charging circuit for charging the capacitor to a desired voltage for generating a therapeutic waveform, comprising:

charging the capacitor to a first voltage , less than the desired voltage needed to produce the therapeutic waveform;

obtaining a first measurement indicative of a leakage current of the capacitor at the first voltage;

determining if the first measurement indicates that the leakage current that would occur across the capacitor when the capacitor is charged to the desired voltage to produce the therapeutic waveform exceeds a first preselected limit; and charging the capacitor to reform the capacitor when the first measurement indicates that the leakage current that would occur across the capacitor when the capacitor is charged to the desired voltage to produce the therapeutic waveform exceeds the first preselected limit.

24. The method of claim 23, wherein the step of determining whether the first measurement indicates that the leakage current that would occur when the capacitor is charged to the desired voltage exceeds the first preselected limit comprises using empirical data obtained for the capacitor to estimate the leakage current that would occur at the desired voltage based upon the first measurement.

25. The method of claim 23, wherein the step of obtaining the first measurement comprises measuring a voltage drop from the first voltage over a preselected time interval and then using the voltage drop to determine the leakage current occurring when the capacitor is charged to the first voltage.

26. The method of claim 23, wherein the step of charging the capacitor to reform the capacitor comprises charging the capacitor to a second voltage greater than the first voltage.

27. The method of claim 26, wherein the step of charging the capacitor to the second voltage comprises charging the capacitor to the desired voltage.

28. The method of claim 26, further comprising the step of obtaining a second measurement indicative of the leakage current of the capacitor at the second voltage.

29. The method of claim 28, wherein the step of obtaining the second measurement comprises measuring a voltage drop from the second voltage over a preselected time interval and then using the voltage drop to measure the leakage current occurring when the capacitor is charged to the second voltage.

30. The method of claim 28, further comprising the step of determining whether the second measurement indicates that the leakage current that would occur when the capacitor is charged to the desired voltage exceeds a second preselected limit.

31. The method of claim 30, wherein the step of determining whether the second measurement indicates that the leakage current that would occur when the capacitor is charged to the desired voltage exceeds second preselected limit comprises using empirical data obtained for the capacitor to estimate the leakage current that would occur at the desired voltage based upon the second measurement.

32. The method of claim 30, further comprising the step of supplementally reforming the capacitor upon determining that the second measurement indicates that the leakage current that would occur when the capacitor is charged to the desired voltage still exceeds the second preselected limit.

33. The method of claim 32, wherein the step of supplementally reforming the capacitor comprises retaining the capacitor in a charged state after charging the capacitor to the second voltage for a preselected period of time.

34. The method of claim 33, wherein the step of supplementally reforming the capacitor comprises retaining the capacitor in the charged state for an hour after charging the capacitor to the second voltage.

35. The method of claim 32, further comprising the steps of:

recharging the capacitor to the second voltage upon completion of the supplementally reforming step;

re-obtaining the second measurement indicative of the leakage current occurring when the capacitor is recharged to the second voltage;

repeating the supplementally reforming step if the re-obtained second measurement still indicates that the leakage current that would occur if the capacitor is charged to the desired voltage exceeds the second preselected limit.

* * * * *